United States Patent [19]
Kelley

[11] Patent Number: 6,071,266
[45] Date of Patent: Jun. 6, 2000

[54] LUBRICIOUS MEDICAL DEVICES

[76] Inventor: Donald W. Kelley, 608 N. Palestine, Athens, Tex. 75751

[21] Appl. No.: 09/178,018

[22] Filed: Oct. 23, 1998

Related U.S. Application Data

[63] Continuation-in-part of application No. 08/842,058, Apr. 23, 1997
[60] Provisional application No. 60/017,339, Apr. 26, 1996.
[51] Int. Cl.⁷ ...................................................... A61M 5/32
[52] U.S. Cl. .............................................................. 604/265
[58] Field of Search ..................................... 604/264, 265, 604/523, 536

*Primary Examiner*—Wynn Wood Coggins
*Assistant Examiner*—Deborah Blyveis
*Attorney, Agent, or Firm*—Donald W. Erickson; Jacqueline S. Larson

[57] ABSTRACT

Lubricious medical devices such as catheters and stents which minimize friction and retain lubricity and dimensional properties for a long period of time. The devices are made by coextrusion wherein the inner layer is a hydrophobic polymer and the outer layer is a blend of a hydrophilic polymer and hydrophobic polymer. Devices made by extrusion of a blend of hydrophobic polymer with a blend of hydrophobic/hydrophilic polymer are described also.

10 Claims, No Drawings

LUBRICIOUS MEDICAL DEVICES

This is a continuation-in-part of Application Ser. No. 08/842,058, filed Apr. 23, 1997, which claims the benefit of U.S. Provisional Application Ser. No. 60/017,339, filed Apr. 26, 1996.

It is desirable for a medical device (catheter, stent, introducer, etc.) which is to be used in the health care of animals (human, pet, work or other animal) to produce the minimal amount of friction possible. It is obvious that a device penetrating a body which produces high friction will create many undesirable results, e.g., irritation, discomfort, trauma, agitation of existing conditions, etc.

It is also obvious that a medical device which is functioning within a device (i.e., catheter through an introducer) that has a high coefficient of friction produces greater pressure and stresses increasing the risk of the undesirable results as above.

It is also obvious that a device which has foreign substances (i.e., calcification, protein adhesion etc.) adhering to it could produce some of the same stated undesirable results upon removal from the body.

It is a purpose of this invention to provide medical devices which will retain their lubricity and physical properties for a long period of time while in continuous contact with body fluids.

It is further a purpose of this invention to provide medical devices which will retain their lubricity and physical properties for a long period of time while in continuous contact with body fluids.

It is further a purpose of this invention to provide devices that have biocompatability, good ascetic appearances, feel and handling characteristics.

There are numerous devices that attempt to accomplish the purposes of this invention; they, however, fall short in one or more of the following areas.

1. They are not sufficiently lubricious throughout the procedure for which they are designed.
2. They do not retain lubricity for long periods of time or extended use.
3. The hydrophilic coating does not adhere to the device resulting in flaking.
4. Some will swell and not hold dimensions when exposed to hydrophilic fluids.
5. Some coatings do not have even or uniform application.
6. Some do not provide long lasting barrier protection to prevent foreign substances from sticking and building up on its surface.

In accordance with this invention a lubricious medical device can be manufactured that:

1. Has a very low coefficient of friction when contact is made with a hydrophilic medium (water, body fluids, etc.)
2. The hydrophilic lubricious polymer is an homogeneous integral part of the device.
3. Will retain its lubricity for a long period of time when in contact with a hydrophilic substance.
4. Will retain its dimensional properties after long exposure to hydrophilic liquid.
5. Will prevent salts build up or adhesion to its surface.
6. Has good biocompatability, ascetic appearances, feel and handling characteristics.

In accordance with the present invention, a hydrophobic polymer, a hydrophilic lubricating polymer and heat and light stabilizers are blended together. This blend is mixed homogeneously in a melt state, cooled and pelletized. A dual extrusion is then carried out by using a hydrophobic polymer as a first or inner part of the extrusion and the pelletized blend as a second or outer part of the extrusion. The extrusion can be used to produce a film, tube or other profile. The extrusion may also be extruded into a mold or extruded into a sheet and vacuum formed.

Hydrophobic polymers that can be used, by way of example, are polyethylene, ethylene acrylates, ethylene vinyl acetate, thermoplastic polyurethane, styrene and co-polymers, silicones, etc.

Hydrophilic polymers that can be used, by way of example, are polyethylene glycol, poly(ethylene oxide) and polyvinylpyrrolidone, etc.

Suitable stabilizers include vitamin E, zinc oxide, etc.

Percentages are by weight, temperature in Fahrenheit.

EXAMPLE 1

COMPOUND A

| Ingredients | Percentages |
| --- | --- |
| Ethylene vinyl acetate (Elvax 150) | 48.95 |
| Poly(ethylene oxide) (PolyOx WSRN-12K) | 48.95 |
| Vitamin E | .10 |
| Zinc oxide | 2.00 |

These ingredients are blended together and compounded with a 24 to 1 single screw extruder, utilizing a single stage mixing screw.

Extruder Profile

| Die head | zone 4 | zone 3 | zone 2 | zone 1 | |
| --- | --- | --- | --- | --- | --- |
| 240 | 250 | 265 | 275 | 275 | 240 degrees. |

Screen Pack I-40, I-60, I-80, 2-200, 1-80

The blend is extruded into strands and pelletized.

A second extruder is now placed in line, with both extruders connected to a single crosshead dual tube die. Extruder #1 is charged with a hydrophobic polymer (Ethylene vinyl acetate sold as Elvax 650). Extruder #2 is charged with Compound A. In this example, extruder #1 extrudes the inner portion of the tube and extruder #2 extrudes the outer portion of the tube. The ratios of inner to outer portions may be varied by adjusting the output of either extruder by increasing or lowering screw speed. In Example 1 the ratio of inner and outer portions is one to one. In order to meet the objectives of this example, the hydrophilic portion (Compound A) is a minimum of about 25 percent of the tube. The coextrusion profile is the same for both extruders as in compounding.

A stent made by Example 1 was tested as follows:

1. A stent made from polyurethane and a stent made by Example 1 were ground to the exact same size (O.D. 0.088+0.0005—None). The surfaces were smooth with no irregularities when felt by hand and viewed with a Deltronic optical comparitor.
2. A PVC tube sized (I.D. 0.091/0.092) so as the stent had sufficient room to move freely through the inside of the tube was bent. The tube was held in position by attaching it to a ridged strip of plastic tape material.
3. The stents were placed in room temperature water for 30 seconds, removed and placed in the PVC tube fixture.
4. The stent was then attached to an Ametek Force Guage.

5. The PVC fixture was then pulled until the stent was completely through the fixture.

| Urethane Stent | Example 1 Stent |
|---|---|
| 0.53 lbs. | 0.38 lbs. |
| 0.64 lbs. | 0.20 lbs. |
| 0.49 lbs. | 0.25 lbs. |
| 0.55 lbs. Average | 0.28 lbs. Average |

A stent made by Example 2 demonstrates the objectives of the invention.

EXAMPLE 2

COMPOUND B

| Ingredients | Percentages |
|---|---|
| Steron 840 A | 83.9 |
| PolyOx 308 | 12.0 |
| Vitamin E | .1 |
| Zinc Oxide | 4.0 |

This formula is compounded as in Example 1. Thereafter this formula may be dual extruded with Steron 840A as the hydrophobic polymeric inner portion of the tube in the ratio required to obtain the physical properties desired. The ratio for hydrophilic COMPOUND B to a hydrophobic polymer Steron 840A can be about 75–25 parts COMPOUND B to about 25–75 parts Steron 840A.

EXAMPLE 3

COMPOUND C

| Ingredients | Percentages |
|---|---|
| Estane 5714F | 70.0 |
| Polyethylene glycol 1450 NF | 10.0 |
| PolyOx N750 NF | 20.0 |

Mixing procedure for COMPOUND C:

1. The polyethylene glycol 1450 NF is heated to a liquid state (250 degrees F.) and added to the Estane 5714F pellets while mixing.
2. The PolyOx N750 NF is added to the Estane/polyethylene glycol blend while it is still warm and the polyethylene glycol is soft. This causes the PolyOx to stick to the pellets.

Extruder Profile

| Die | Head | zone 4 | zone 3 | zone 2 | zone 1 | |
|---|---|---|---|---|---|---|
| 315 | 315 | 315 | 315 | 315 | 315 | degrees |

Thereafter this formula may be coextruded with a hydrophobic polymer with the ratios falling within about 50–75 parts COMPOUND C to about 50–25 parts hydrophobic polymer. Coextrusion utilizes the same profile for each extruder as in compounding.

EXAMPLE 4

Using COMPOUND A as in Example 1 and High Density Polyethylene as the hydrophobic polymer in place of polyurethane, a stiff lubricious catheter can be constructed. Ratios can fall within about 25–50 parts COMPOUND A to about 75–50 parts High Density Polyethylene.

Coextrusion Profile

Extruder #1 (HDPE)

| Die | Head | zone 4 | zone 3 | zone 2 | zone 1 | |
|---|---|---|---|---|---|---|
| 240 | 240 | 300 | 350 | 350 | 350 | degrees |

Extruder #2

| zone 4 | zone 3 | zone 2 | zone 1 | |
|---|---|---|---|---|
| 265 | 275 | 275 | 240 | degrees |

EXAMPLE 5

Utilizing Example 1 a sheet was coextruded. Washers were cut out to fit an introducer. When a standard wet catheter is passed through the introducer, the washer acts as a lubricating bearing making it much easier to move the catheter in and out.

EXAMPLE 6

COMPOUND D

| Ingredients | Percentages |
|---|---|
| Polyvinylpyrrolidone (K-90) | 20.0 |
| Anhydrous glycerin | 10.0 |
| Ethylene vinyl acetate (Elvax 150) | 67.9 |
| Vitamin E | .1 |
| Zinc oxide | 2.0 |

Mixing procedure:

1. Ethylene vinyl acetate pellets are coated with the liquid ingredients, glycerin and vitamin E.
2. The powdered ingredients are then added while mixing. The powder will stick to the pellets rendering a dry blend.
3. The blend is then compounded in the extruder as in Example 1. The extruder profile is the same as in Example 1.

COMPOUND D may be coextruded with the hydrophobic polymer (ethylene vinyl acetate) in the same ratios as Example 1. The extruder profiles are also the same as in Example 1.

EXAMPLE 7

COMPOUND E

| Ingredients | Percentages |
|---|---|
| Exact Plastomer 4003 | 43.95 |
| PolyOx WSR N-750 | 43.95 |
| Vitamin E | .10 |
| Zinc oxide | 2.00 |
| Carbowax 1750 | 10.00 |

Mixing procedure;

1. The Exact Plastomer 4003, PolyOx WSR N-750, vitamin E and zinc oxide are mixed so as to be homogeneous.

2. The Carbowax 1750 is heated to a liquid state.

3. While the blend of polymers and stabilizers are mixing, the liquid Carbowax is added.

4. The mixing is continued until a homogeneous blend is achieved.

5. This blend is compounded as in Example 1 except the extruder profile is as follows:

| Die | Head | zone 4 | zone 3 | zone 2 | zone 1 |         |
|-----|------|--------|--------|--------|--------|---------|
| 275 | 275  | 275    | 260    | 250    | 250    | degrees |

EXAMPLE 8

Compound E can be extruded with a blend of hydrophobic polymers. An example of such a blend is Exact Plastomer 4003 and Ultra High Molecular Weight Silicone Compound MB-50-002. The hydrophobic polymer blend can be mixed in the following ratios:

| Exact 4003 | 95 to 5 parts |
|------------|---------------|
| MB-50-002  | 5 to 95 parts |

Specific:

| Exact 4003 | 80.0 parts |
|------------|------------|
| NB-50-002  | 20.0 parts |

This hydrophobic polymer blend is now mixed with Compound E. The ratios may be as follows:

| Compound E               | 20 to 50 parts |
|--------------------------|----------------|
| Hydrophobic Polymer Blend | 50 to 80 parts |

Specific:

| Compound E               | 35.0 parts |
|--------------------------|------------|
| Hydrophobic Polymer Blend | 65.0 parts |

This example may be extruded into a single profile which provides lubrication on all surfaces. The extrusion profile is as follows.

| Die | Head | zone 4 | zone 3 | zone 2 | zone 1 |         |
|-----|------|--------|--------|--------|--------|---------|
| 305 | 300  | 300    | 290    | 290    | 280    | degrees |

Screen Pack 1-40, I-60, I-80, 2-200, 1-80

Head Pressure 3,500 to 4,500 psi

Exact Plastomer 4003 is a polyethylene supplied by Exxon, Houston, Tex. Silicone MB-50-002 is supplied by Dow Corning, Midland, Mich. Elvax is supplied by DuPont, Wilmington, Del. Estane is a polyurethane supplied by B.F. Goodrich, Cleveland, Ohio. Steron is an SB copolymer supplied by Firestone, Akron, Ohio. PolyOx and Carbowax are products of Union Carbide, Danbury, Conn. Polyvinylpyrrolidone K-90 is supplied by International Specialty Products, Wayne, N.J.

EXAMPLE 9

Swelling Evaluation

Stents were made in accordance with the present invention using the procedure of Example 1 and the hydrophilic/hydrophobic polymer blend of Example 7. Thirty samples of the stent were cut to equal length and three each placed into a test tube filled with distilled water. The outside diameter, inside diameter and length of each stent specimen was measured prior to placing in the test tubes. The test tubes were held at room temperature. Over one month, at three day intervals a test tube was opened and the three specimens were measured, averaged and recorded. All measurements were taken with an optical comparator. The average percentage of swell for the measurements was 3.4 outside diameter, 0.4 inside diameter and 0.0 length. This evaluation demonstrates the excellent dimensional properties retained by stents in accordance with the present invention.

What is claimed is:

1. A lubricious medical device having a very low coefficient of friction which comprises:

a laminate of two polymeric layers wherein one layer constitutes the inner layer and one layer constitutes the outer layer;

said inner layer being formed of a hydrophobic polymer;

said outer layer being formed of a lubricious polymeric blend of a hydrophilic polymer and a hydrophobic polymer;

said polymeric blend constituting not less that about 25 percent of the thickness of the laminate;

said hydrophilic polymer constituting not less that about 25 percent of the lubricious polymeric blend; and said medical device having the property of retaining its original dimensional properties after prolonged exposure to hydrophilic liquid.

2. The medical device according to claim 1 wherein the device is a catheter.

3. The medical device according to claim 2 wherein the amount of hydrophilic polymer is a is about 50 percent of the lubricious polymeric blend.

4. The medical device according to claim 3 wherein the lubricious polymeric blend constitutes about 50 percent of the thickness of the laminate.

5. The medical device according to claim 2 wherein the polymeric blend contains about 50 percent hydrophilic polymer and the laminate is formed of about 50 percent lubricious polymeric blend as the outer layer.

6. The medical device according to claim 2 wherein said polymeric blend is a blend of ethylene vinyl acetate and poly(ethylene oxide) and polyvinylpyrrolidone.

7. The medical device according to claim 2 wherein the hydrophilic polymer is selected from the group consisting of polyethylene glycol poly(ethylene oxide) and polyvinylpyrrolidone.

8. The medical device according to claim 7 wherein the hydrophobic polymer is ethylene vinyl acetate.

9. The medical device according to claim 7 wherein the hydrophobic polymer is polyethylene.

10. The medical device according to claim 7 wherein the hydrophobic polymer of the inner layer is high density polyethylene.

* * * * *